(12) United States Patent
Chambers et al.

(10) Patent No.: US 6,689,888 B2
(45) Date of Patent: Feb. 10, 2004

(54) PROCESSES AND INTERMEDIATES USEFUL IN PREPARING β₃-ADRENERGIC RECEPTOR AGONISTS

(75) Inventors: Robert J. Chambers, Mystic, CT (US); Robert W. Dugger, Stonington, CT (US); Ming Kang, Salem, CT (US); Yong Tao, Salem, CT (US); John W. Wong, East Lyme, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/370,793

(22) Filed: Feb. 20, 2003

(65) Prior Publication Data

US 2003/0199046 A1 Oct. 23, 2003

Related U.S. Application Data

(60) Provisional application No. 60/360,286, filed on Feb. 27, 2002.

(51) Int. Cl.⁷ .................. C07D 417/02; C07D 413/02; C07D 401/02
(52) U.S. Cl. ................. 546/269.7; 546/271.4; 546/275.4; 546/271.1; 546/272.1
(58) Field of Search ........................ 546/269.7, 271.1, 546/271.4, 272.1, 275.4

(56) References Cited

U.S. PATENT DOCUMENTS

| | | | | |
|---|---|---|---|---|
| 4,358,455 A | 11/1982 | Atkinson et al. | ........... | 424/263 |
| 4,478,849 A | 10/1984 | Ainsworth et al. | ......... | 424/285 |
| 4,835,164 A | 5/1989 | Shanklin et al. | ............ | 514/317 |
| 4,918,091 A | 4/1990 | Cantello et al. | ............ | 514/369 |
| 5,019,578 A | 5/1991 | Fisher et al. | ................ | 514/275 |
| 5,030,640 A | 7/1991 | Fisher et al. | ................ | 514/339 |
| 5,051,423 A | 9/1991 | Lis et al. | .................... | 514/252 |
| 5,108,992 A | 4/1992 | Lawrence et al. | ............ | 514/30 |
| 5,135,932 A | 8/1992 | Hauel et al. | ................. | 514/253 |
| 5,153,210 A | 10/1992 | Ainsworth et al. | ......... | 514/369 |
| 5,393,779 A | 2/1995 | Holloway et al. | .......... | 514/539 |
| 5,541,197 A | 7/1996 | Fisher et al. | ................ | 514/311 |
| 5,684,022 A | 11/1997 | Shuto et al. | ................. | 514/335 |
| 5,767,133 A | 6/1998 | Dow et al. | .................. | 514/339 |
| 5,776,983 A | 7/1998 | Washburn et al. | .......... | 514/605 |
| 5,840,738 A | 11/1998 | Bell et al. | ................... | 514/359 |
| 5,843,972 A | 12/1998 | Dow et al. | .................. | 514/367 |

(List continued on next page.)

FOREIGN PATENT DOCUMENTS

| | | | | |
|---|---|---|---|---|
| EP | 0236624 | 8/1993 | ......... | C07D/309/38 |
| EP | 0543662 | 9/1996 | ......... | C07C/217/22 |
| EP | 0764632 | 3/1997 | ......... | C07C/233/52 |
| EP | 0882707 | 12/1998 | ......... | C07C/311/37 |
| EP | 1236723 | 9/2002 | ......... | C07D/295/22 |
| WO | WO 9000548 | 1/1990 | ......... | C07D/223/58 |
| WO | WO 9804526 | 2/1998 | ......... | C07D/209/04 |
| WO | WO 9821184 | 5/1998 | ......... | C07D/213/75 |
| WO | WO 9942455 | 8/1999 | ......... | C07D/277/40 |
| WO | WO 9945006 | 9/1999 | ......... | C07D/413/14 |
| WO | WO 0040560 | 7/2000 | ......... | C07D/213/80 |
| WO | WO0179180 | 10/2001 | ......... | C07D/233/00 |
| WO | WO0194337 | 12/2001 | ......... | C07D/319/06 |
| WO | WO 0232897 | 4/2002 | ......... | C07D/417/14 |
| WO | WO 0248134 | 6/2002 | ......... | C07D/311/58 |

OTHER PUBLICATIONS

U.S. patent 2002–032222 published Mar. 14, 2002 Malamas, et al.

U. patent 2003–055079 published Mar. 20, 2003 Malamas, et al.

Japan Abstract 2001–017193.

Bailey, et al., "Selective Biohydroxylation of 1–substituted adamantanes using *Absidia cylindrospora*", *Chem. Commun.*, Volume pp. 1833–1834 (1996).

Ridyard, et al., "Site Selective Oxidation of Tricyclo [3.3.1.1³,⁷] decane (adamantine) and some of its derivatives using fungi of the *genus Absidia*", *J. Chem. Soc.*, vol. 2, pp. 1811–1818.

Davies, et al., "Microbial Hydroxylation of Cyclohexylcyclohexane: Synthesis of an analogue of leukotriene–B3", *Tetrahedron Letters*, vol. 27 (9), pp. 1089–1092 (1986).

U.S. Application No. 10/373119 filed on Feb. 24, 2003 entitled "β3 Adrenergic Receptor Agonists" having Attorney Docket No. PC23110A.

U.S. Application No. 10/373473 filed on Feb. 25, 2003 entitled "β3–Adrenergic Receptor Agonist Salt, Formulations, and Uses Thereof" having Attorney Docket No. PC23282A.

U.S. Application No. 10/373492 filed on Feb. 25, 2003 entitled "B3–Adrenergic Receptor Agonist Crystal Forms, Processes for the Production Thereof, and Uses Thereof" having Attorney Docket No. PC23283A.

Primary Examiner—C. S. Aulakh
Assistant Examiner—P. Tuck
(74) Attorney, Agent, or Firm—Peter C. Richardson; Gregg C. Benson; Arlene K. Musser

(57) ABSTRACT

The present invention provides processes useful in the preparation of certain β₃-adrenergic receptor agonists of the structural formula

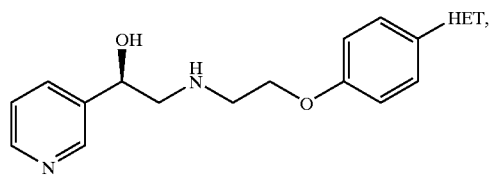

the pharmaceutically acceptable salts thereof, and the hydrates of said pharmaceutically acceptable salts, wherein HET is as described herein. The invention further provides intermediates useful in the preparation of such agonists, and processes useful in the production of such intermediates.

6 Claims, No Drawings

U.S. PATENT DOCUMENTS

| | | |
|---|---|---|
| 5,859,044 A | 1/1999 | Dow et al. .................. 514/419 |
| 5,977,124 A | 11/1999 | Dow .......................... 514/272 |
| 6,001,856 A | 12/1999 | Dow .......................... 514/330 |
| 6,008,361 A | 12/1999 | Wright ....................... 546/307 |
| 6,090,942 A | 7/2000 | DeVries et al. ............... 546/14 |
| 6,187,809 B1 | 2/2001 | Miyoshi et al. ............. 514/443 |
| 6,251,925 B1 | 6/2001 | Donaldson et al. ......... 514/354 |
| 6,265,581 B1 | 7/2001 | Bell et al. ................ 546/277.4 |
| 6,291,489 B1 | 9/2001 | DeVries et al. ............. 514/352 |
| 6,291,491 B1 | 9/2001 | Weber et al. ............... 514/357 |
| 6,297,382 B1 | 10/2001 | Scott ....................... 546/276.4 |
| 6,441,181 B1 | 8/2002 | Scott ....................... 546/276.4 |
| 6,451,587 B1 | 9/2002 | Burns et al. ................ 435/280 |
| 6,465,501 B2 | 10/2002 | Malamas et al. ........... 514/376 |
| 6,566,377 B2 * | 5/2003 | Day et al. .................. 514/340 |

* cited by examiner

PROCESSES AND INTERMEDIATES USEFUL IN PREPARING β₃-ADRENERGIC RECEPTOR AGONISTS

This application claims the benefit of U.S. Provisional Application No. 60/360,286 filed on Feb. 27, 2002 and incorporated herein by reference in its entirety.

FIELD OF THE INVENTION

The present invention provides processes and intermediates useful in the preparation of certain β₃-adrenergic receptor agonists, which agonists are useful in treating, inter alia, hypoglycemia, and obesity, and for increasing the content of lean meat in edible animals.

BACKGROUND OF THE INVENTION

Diabetes mellitus is characterized by metabolic defects in the production and utilization of carbohydrates which result in the failure to maintain appropriate blood sugar levels. The results of these defects include, inter alia, elevated blood glucose or hyperglycemia. Research in the treatment of diabetes has centered on attempts to normalize fasting and postprandial blood glucose levels. Current treatments include administration of exogenous insulin, oral administration of drugs, and dietary therapies.

Two major forms of diabetes mellitus are recognized. Type 1 diabetes, or insulin-dependent diabetes mellitus (IDDM), is the result of an absolute deficiency of insulin, the hormone that regulates carbohydrate utilization. Type 2 diabetes, or non-insulin-dependent diabetes mellitus (NIDDM), often occurs with normal, or even elevated, levels of insulin and appears to be the result of the inability of tissues to respond appropriately to insulin. Most Type 2 diabetic patients are also obese.

Obesity constitutes a major health risk that leads to mortality and incidence of Type 2 diabetes mellitus, hypertension, and dyslipidemia. In the United States, more than 50% of the adult population is overweight, and almost 25% of the population is considered to be obese. The incidence of obesity is increasing in the United States at a three-percent cumulative annual growth rate. While the vast majority of obesity occurs in the United States and Europe, the prevalence of obesity is also increasing in Japan. Furthermore, obesity is a devastating disease which can also wreak havoc on an individual's mental health and self-esteem, which can ultimately affect a person's ability to interact socially with others. Unfortunately, the precise etiology of obesity is complex and poorly understood, and societal stereotypes and presumptions regarding obesity only tend to exacerbate the psychological effects of the disease. Because of the impact of obesity on society in general, much effort has been expended in efforts to treat obesity, however, success in the long-term treatment and/or prevention thereof remains elusive.

In response thereto, a diversity of therapeutic agents have been developed including, for example, β₃-adrenergic receptor activators/agonists. Activation of β₃-adrenergic receptors is known to stimulate lipolysis (e.g., the breakdown of adipose tissue triglycerides into glycerol and fatty acids) and metabolic rate (energy expenditure), thereby promoting the loss of fat mass. Accordingly, compounds that stimulate β₃-adrenergic receptors are useful as anti-obesity agents. In addition, compounds that are β₃-adrenergic receptor agonists have hypoglycemic activity, however, the precise mechanism of this effect is presently unknown.

Commonly assigned U.S. Provisional Application No. 60/242,274, filed Oct. 20, 2000, and incorporated herein by reference, discloses certain β₃-adrenergic receptor agonists of the general structural Formula (I),

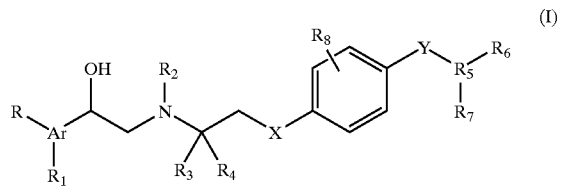

(I)

the stereoisomers and prodrugs thereof, and the pharmaceutically acceptable salts of the compounds, stereoisomers, and prodrugs.

The instant invention provides processes useful in the preparation of certain β₃-adrenergic receptor agonists of structural Formula (I), which agonists are disclosed in detail hereinbelow. The invention further provides intermediates useful in the preparation of such agonists, and processes useful in the production of such intermediates.

SUMMARY OF THE INVENTION

The present invention provides processes useful in the preparation of certain β₃-adrenergic receptor agonists of the structural formula

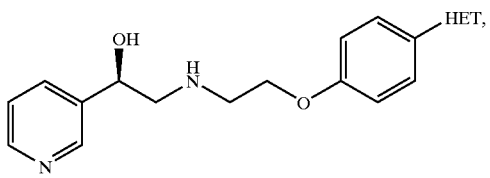

the pharmaceutically acceptable salts thereof, and the hydrates of said pharmaceutically acceptable salts, wherein HET is as defined hereinbelow. The invention further provides intermediates useful in the preparation of such agonists, and processes useful in the production of such intermediates.

DETAILED DESCRIPTION

The present invention provides processes useful in the preparation of certain β₃-adrenergic receptor agonists of the structural formula

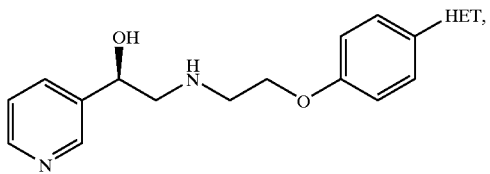

the pharmaceutically acceptable salts thereof, and the hydrates of said pharmaceutically acceptable salts, wherein HET is a heterocyclic moiety selected from the group consisting of oxazolyl, pyrazolyl, and thiazolyl.

The invention further provides intermediates useful in the preparation of such agonists, and processes useful in the production of such intermediates. These enantioselective processes, to be described in greater detail hereinbelow, proceed in a convergent manner, utilize a minimum number of starting materials, and furnish products retaining an overall high degree of enantiospecificity.

In one aspect of the present invention, there is provided a process for preparing a compound of the structural formula

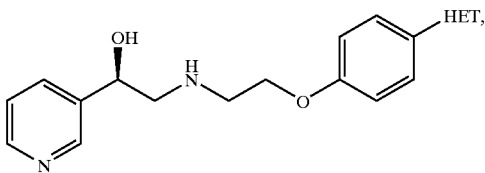

a pharmaceutically acceptable salt thereof, or a hydrate of said pharmaceutically acceptable salt, which process comprises the steps of:

(a) reducing an α-bromoketone derivative of the structural formula

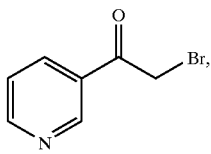

or an acid addition salt thereof, to form an (R)-bromoalcohol derivative of the structural formula

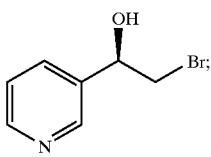

(b) protecting the (R)-bromoalcohol derivative of Step (a) to form an O-protected derivative of the structural formula

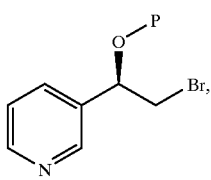

(c) condensing the O-protected derivative of Step (b) with an amine of the structural formula

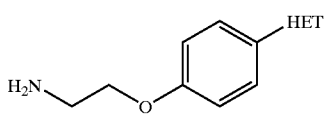

to produce an O-protected derivative of the structural formula

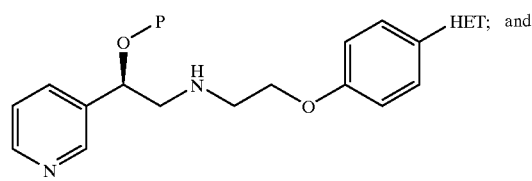

(d) deprotecting the O-protected derivative of Step (c) to form the compound of the structural formula

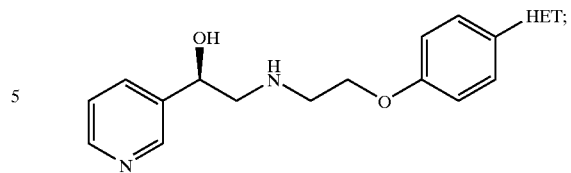

wherein:

HET is a heterocyclic moiety selected from the group consisting of oxazolyl, pyrazolyl, and thiazolyl; and P is an O-protecting moiety selected from the group consisting of —SiR$^1$R$^2$R$^3$, —CH$_2$Ph, —CH$_2$(p-CH$_3$OPh), —CH(OCH$_2$CH$_3$)CH$_3$, and

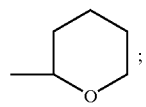

wherein R$^1$, R$^2$, and R$^3$ are, independently, (C$_1$–C$_6$)alkyl, or phenyl.

Preferably, P is —SiR$^1$R$^2$R$^3$, and HET is a heterocyclic moiety selected from the group consisting of 2-oxazolyl, 4-oxazolyl, 3-pyrazolyl, 4-pyrazolyl, 2-thiazolyl, and 4-thiazolyl. The process wherein P represents —SiR$^1$R$^2$R$^3$, wherein R$^1$ and R$^2$ are both —CH$_3$, and R$^3$ is —C(CH$_3$)$_3$ is especially preferred.

The stereospecific reduction step, denoted hereinabove as Step (a), preferably employs a fungal reducing agent. Generally, the use of fungal and/or microbial reducing agents in the stereospecific biotransformation of pharmaceutical intermediates is known. See, for example, R. N. Patel, Advances in Applied Microbiology, 43, 91–140 (1997). Specifically, the stereospecific reduction of α-haloketones with various microorganisms is also generally known. See, for example, R. N. Patel, et al., JAOCS, 75 (11), 1473–1482 (1998), which discloses the use of *Agrobacterium tumefaciens* ATCC 15955, *Alcaligenes eutrophus* ATCC 17697, *Arthrobacter petroleophagus* ATCC 21494, *Debaryomyces hansenil* ATCC 66354, *Mycobacterium* sp. ATCC 29676, *Rhodococcus rhodochorous* ATCC 14347, *Hansenula anomala* SC 13833, *H. anomala* ATCC 16142, *H. saturnus* SC 13829, and *Spingomonas paucimobilis* SC 16113 in the stereospecific reduction of α-bromoketones. The fungal reducing agent utilized in reduction Step (a) of the instant invention preferably comprises *Absidia cylindrospora* ATCC 22751 (American Type Culture Collection, Rockville, Md.). The aforementioned reduction step affords the corresponding (R)-bromoalcohol in a highly enantioselective yield, i.e. >90% enantiomeric excess. Preferably, the (R)-bromoalcohol so formed in the stereospecific reduction Step (a) is then isolated, either as a free base, or an acid addition salt thereof.

The (R)-bromoalcohol product formed in the stereospecific reduction Step (a) is then O-protected. Synthetic methods of protecting alcohol functional groups are well-known to one of ordinary skill in the art and may comprise, for example, functionalizing the alcohol as a silyl, ether, or ester derivative thereof. Although any conventional O-protecting group that is compatible with the reaction conditions employed in subsequent synthetic steps may be employed in the processes of the present invention, the (R)-bromoalcohol product of Step (a) is preferably protected as an O-silyl ether derivative. The preferred O-silylation step, generically denoted hereinabove as Step (b), may be effected according to standard methodologies that will be known to one of ordinary skill in the art. Such preferred O-silylation is typically effected by treatment of the (R)-bromoalcohol with an appropriately substituted silylating agent. Such silylating agents may comprise, for example, those silyl derivatives of the formula $R^1R^2R^3Si$—X, wherein X comprises an appropriate leaving group. Preferably, the silylating agent comprises a reactant of the formula $R^1R^2R^3Si$—X, wherein X is a leaving group selected from the group consisting of halogen (e.g., chloro or bromo), cyano, imidazolyl, triflate (trifluoromethanesulfonate), and the like. However, other silylating agents, that may be employed in accordance with the processes of the instant invention, will also be known to one of ordinary skill in the art. Preferably $R^1$, $R^2$, and $R^3$, within the definition of the protected alcohol moiety —$OSiR^1R^2R^3$ are, independently, $(C_1-C_6)$alkyl, or phenyl. The O-silyl ether derivative wherein $R^1$ and $R^2$ are both —$CH_3$, and $R^3$ is —$C(CH_3)_3$ is especially preferred.

Typically, O-silylation is effected by condensing the alcohol to be protected with the silylating agent in the presence of a suitable organic base, for example, an alkylamine, such as triethylamine, N,N-diisopropylethylamine (Hunig's base), or a heterocyclic amine, such as imidazole or diazabicyclo[5.4.0]undec-7-ene (DBU), in a halogenated hydrocarbon solvent, such as dichloromethane. Alternatively, a polar, aprotic solvent, such as dimethylformamide or dimethylsulfoxide may also be employed. With respect to the O-silylation reaction of the present invention, dimethylformamide is preferred. Typically, such silylation is effected by stirring the reactants at, or about, room temperature for an extended period of time, i.e., overnight. However, such silylation may also be performed at greater, or lesser, than ambient temperature, where appropriate.

For a detailed discussion of methods of protecting alcohol functional groups, including those preferred methods employing silylating agents see, for example, T. W. Greene, et al., Protective Groups in Organic Synthesis, John Wiley & Sons, New York, N.Y. (1991), and the references cited therein.

The O-protected derivative so formed in Step (b) is then condensed in Step (c) with an amine of the structural formula

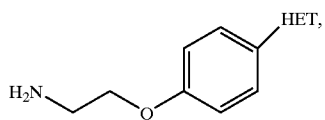

wherein HET is as defined hereinabove, to provide a product of the structural formula

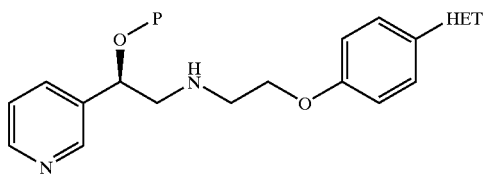

The aforementioned condensation Step (c) may be carried out under standard reaction conditions known to one of ordinary skill in the art. Preferably, the protected (R)-bromoalcohol and the amine are condensed in the presence of a suitable organic base, for example, an alkylamine, such as triethylamine or N,N-diisopropylethylamine (Hunig's base), in a polar, aprotic solvent, such as dimethylsulfoxide. Such condensation is typically effected at an elevated temperature, preferably in the general range of from about 40° to about 120V C. Preferably $R^1$, $R^2$, and $R^3$, within the definition of the preferred moiety —$SiR^1R^2R^3$ are, independently, $(C_1-C_6)$alkyl, or phenyl. The process where $R^1$ and $R^2$ are both —$CH_3$, and $R^3$ is —$C(CH_3)_3$ is especially preferred. The amines employed in condensation Step (c) may be prepared according to the exemplary processes to be described in detail hereinbelow.

The deprotection step, denoted hereinabove as Step (d), may be performed according to standard methods that will be known to one of ordinary skill in the art. The preferred —O—$SiR^1R^2R^3$ derivative formed in Step (c) is preferably deprotected by the reaction thereof with a suitable alkylammonium fluoride, such as tetrabutylammonium fluoride. Such deprotection may be effected at ambient temperature in an aprotic solvent, for example, tetrahydrofuran. For a detailed discussion of methods of deprotecting O-silyl ethers see, for example, T. W. Greene, et al., supra, and the references cited therein.

The deprotected product of Step (d) is then preferably isolated, either in the form of the free base or, if desired, in the form of a pharmaceutically acceptable salt, or a hydrate of such pharmaceutically acceptable salt. Such isolation may be effected according to well-established methods. Likewise, the pharmaceutically acceptable salt may also be prepared according to known methods including, for example, treatment of the isolated free base with a conjugate organic acid, such as succinic, tartaric, acetic, citric, maleic, methanesulfonic, or p-toluenesulfonic acid, and the like. Alternatively, a conjugate inorganic acid, such as hydrochloric, hydrobromic, sulfuric, or nitric acid, and the like, may also be employed. The tosylate salt, i.e., the p-toluenesulfonic acid salt, abbreviated in the instant description and appendant claims as TsOH, of the deprotected product formed in Step (d) is especially preferred. For purposes of facilitating product isolation and augmenting purity, such salt formation is preferably carried out in a reaction-inert solvent, for example, a non-solvent from which the desired salt precipitates upon formation, or, more preferably, in a solvent from which the formed salt precipitates upon subsequent addition of a non-solvent.

One of ordinary skill in the art will further appreciate that such pharmaceutically acceptable salts may form various hydrated forms thereof, and such hydrated forms are embraced within the scope of the present invention. Hydrates of pharmaceutically acceptable salts may be prepared according to well-known methods including, for example, sublimation, crystallization of the hydrate from a single solvent, formation of the hydrate by evaporation from a binary mixture, vapor diffusion, thermal treatment, and the like. For a detailed discussion of methods of preparing hydrates of pharmaceutically acceptable salts see, for example, J. Keith Guillory, Polymorphism in Pharmaceutical Solids, Chapter 5, "Generation of Polymorphs, Hydrates, Solvates, and Amorphous Solids", pp. 183–219, Marcel Dekker, Inc. (1999).

In another aspect, the instant invention provides a process for preparing a compound of the structural formula

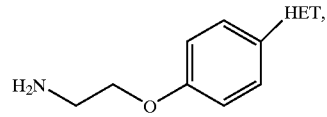

or an acid addition salt thereof, which process comprises the steps of:

(a) functionalizing a compound of the structural formula

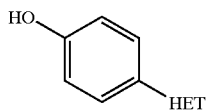

to provide a compound of the structural formula

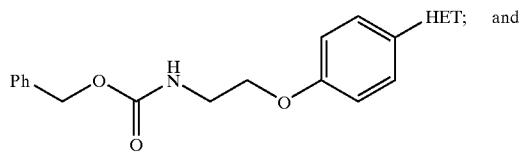 and (b) defunctionalizing the compound so formed in Step (a) to provide the compound of the structural formula

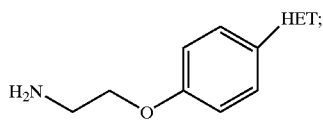

wherein:

HET is a heterocyclic moiety selected from the group consisting of oxazolyl, pyrazolyl, and thiazolyl.

Preferably, HET represents a heterocyclic moiety selected from the group consisting of 2-oxazolyl, 4-oxazolyl, 3-pyrazolyl, 4-pyrazolyl, 2-thiazolyl, and 4-thiazolyl.

In the functionalization step, denoted as Step (a) hereinabove, a phenolic compound of the structural formula

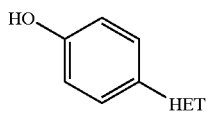

is functionalized to provide a carbamate of the structural formula

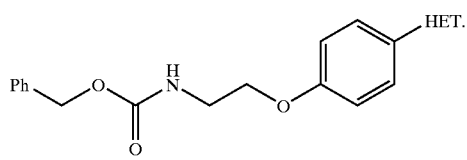

Such phenolic compounds, which may be prepared according to literature methods or, alternatively, according to the synthetic procedures disclosed hereinbelow, are most conveniently functionalized in Step (a) by the reaction thereof with a compound having the general formula $PhCH_2OCONHCH_2CH_2$—Y, wherein Y comprises an appropriate leaving group. Exemplary leaving groups comprise those selected from the group consisting of tosylate (p-toluenesulfonate), mesylate (methanesulfonate), halogen (e.g., bromo, chloro, or iodo), and the like. A mesylate leaving group is generally preferred. The compound of the general formula $PhCH_2OCONHCH_2CH_2$—Y, wherein Y is mesylate may be prepared as disclosed in C. A. Townsend, et al., Tetrahedron 47, 2591 (1991). Functionalization of the phenolic compound is preferably effected in a polar, aprotic solvent, such as dimethylsulfoxide, in the presence of an inorganic base, such as potassium carbonate. The functionalization is typically effected at an elevated temperature, generally in the general range of from about 40° to about 120° C.

The carbamate derivative so formed in functionalization Step (a) hereinabove is then defunctionalized in Step (b) to provide a compound of the structural formula

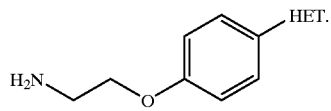

Such defunctionalization of the carbamate product formed in Step (a) may be carried out according to established methods. For example, the carbamate may be defunctionalized by catalytic hydrogenation employing a suitable metallic catalyst, such as a nickel salt, or a complex thereof, a palladium salt, or a complex thereof, or platinum, or a complex thereof. Preferably, the defunctionalization is effected in a polar, protic solvent, such as methanol, using ammonium formate and formic acid in the presence of a metallic catalyst, preferably, palladium on activated carbon. Such defunctionalization is normally performed at an elevated temperature, preferably at the reflux temperature of the solvent employed.

The amine product so formed in Step (b) is then preferably isolated, either in the form of the free base, or in the form of an acid addition salt thereof. Conventional techniques of isolating such free base will be known to one of ordinary skill in the art. Likewise, the acid addition salt of the amine product may also be prepared according to known methods, for example, by treatment of the isolated free base with a conjugate organic acid, such as succinic, tartaric, acetic, citric, maleic, methanesulfonic, or p-toluenesulfonic acid, and the like, or a conjugate inorganic acid, such as hydrochloric, hydrobromic, sulfuric, or nitric acid, and the like. As was previously disclosed hereinabove, facile product isolation and augmented purity are normally best achieved where such salt formation is carried out in a reaction-inert solvent, such as a non-solvent from which the desired salt precipitates upon formation, or in a solvent from which the formed salt precipitates upon subsequent addition of a non-solvent.

In another aspect, the present invention provides the compound of the structural formula

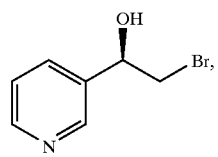

or an acid addition salt thereof.

In another aspect, the present invention provides the compound of the structural formula

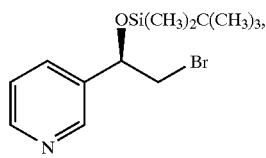

or an acid addition salt thereof.

In yet another aspect, the present invention provides the compound of the structural formula

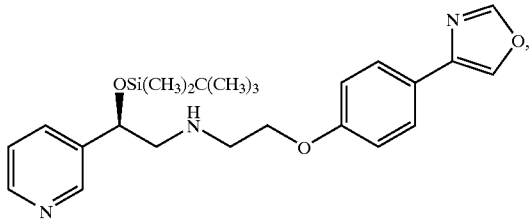

or an acid addition salt thereof.

The present invention is illustrated by the following Examples. It is to be understood, however, that the invention is not limited to the specific details of these examples, as other variations thereof will be known, or apparent in light of the instant disclosure, to one of ordinary skill in the art.

EXAMPLES

Preparation of Intermediates

Preparation of Intermediate (R)-2-Bromo-1-pyridin-3-yl-ethanol:

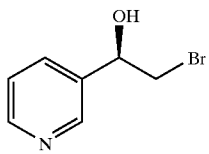

2-Bromo-1-pyridin-3-yl-ethanone hydrobromide (G. B. Davies, et al., Aust. J. Chem., 42, 1735 (1989)) was contacted with cultures of *Absidia cylindrospora* ATCC 22751 grown in Fernbach flasks, or fermentor cultures containing medium A (40 g/l corn steep solids and 20 g/l glucose adjusted to pH 4.85 prior to autoclaving). Fernbach flasks (8), each containing 500 ml of medium A, were inoculated with 5 ml of a seed culture of *Absidia cylindrospora* ATCC 22751. The seed cultures of *A. cylindrospora* were prepared in two 300 ml conical flasks, each containing 40 ml of medium A. These seed cultures were inoculated with a spore stock of *A. cylindrospora* and agitated (210 rpm) for about 24 hours at 29° C. After agitation for a total of about 41 hours at about 29° C., 25 ml of a 20 g/l aqueous solution of the hydrobromide salt of 2-bromo-1-pyridin-3-yl-ethanone was added to each of the Fernbach flask cultures. The flasks were agitated for about an additional 5 hours after which the contents of the flasks were combined and centrifuged to remove solid materials.

Two cultures of *Absidia cylindrospora* ATCC 22751 were grown in fermentors containing 8 l of medium A. The fermentors were each inoculated with a single culture of *A. cylindrospora* grown in Fernbach flasks containing 400 ml of medium A. The Fernbach flask cultures were inoculated with 1.8 ml of spore stock of *A. cylindrospora* ATCC 22751 and agitated (200 rpm) for about 40 hours at about 29° C. After about 24 hours, the two fermentor cultures were treated with an aqueous solution of 2-bromo-1-pyridin-3-yl-ethanone hydrobromide (30 g/l) which resulted in the addition of 8 g of 2-bromo-1-pyridin-3-yl-ethanone hydrobromide to one fermentor, and 16 g of 2-bromo-1-pyridin-3-yl-ethanone hydrobromide to the other fermentor. The fermentor culture that received 8 g of 2-bromo-1-pyridin-3-yl-ethanone hydrobromide was harvested about 24 hours following substrate addition, while the other fermentor was harvested about 5 hours following substrate addition. The contents of both fermentor cultures were centrifuged to remove solid materials.

The supernatant phases from the eight Fernbach flask cultures and the two fermentor cultures were combined, filtered through filter paper, and passed through a column containing 737 g of XAD-16® resin (Rohm & Haas; Philadelphia, Pa.). The resin was then eluted with mixtures of methanol and water (1 l 10% methanol, 1 l 20% methanol, 1 l 30% methanol, 1 l 50% methanol, 3×1 l 80% methanol, and 1 l 100% methanol) and fractions were collected. These fractions were analyzed by HPLC on a 4.6×150 mm Kromasilo C4 column (Phenomenex; Torrance, Calif.), eluting with 10 mM ammonium acetate:acetonitrile (76.5:23.5, v/v) at 1.0 ml/minute, and those fractions found to contain desired product (10% methanol –80% methanol) were pooled, concentrated to remove solvent, and extracted with ethyl acetate. The ethyl acetate extracts were combined, concentrated to about 600 ml, dried with magnesium sulfate, and filtered. This material was divided into several portions and then purified by flash chromatography on silica gel cartridges (1.2×7.5 cm and 4×15 cm, Biotage; Charlottesville, Va.) eluting with ethyl acetate and hexane mixtures containing 0.1% acetic acid(ethyl acetate:hexane:acetic acid; 60:40:0.1; v/v/v). Fractions containing desired product were concentrated to give 1.93 g (9.6%) of title compound as a light yellow oil, $\alpha_D = -16.4°$ (c=0.53, methanol). Chiral HPLC analysis of the product on 4.6×250 mm Chiralcel® OD column (Chiral Technologies; Exton, Pa.) eluting with hexanes:isopropyl alcohol (9:1, v/v) at 1.5 ml/minute revealed an enantiomeric excess of 91.2%.

$^1$HNMR (400 mHz, $d_6$-DMSO): δ 8.55 (d, 1H, J=2.1 Hz), 8.44 (dd, 1H, J=1.7, 4.6 Hz), 7.75 (dd, 1H, J=2.5, 4.2 Hz), 7.33 (m, 1H), 5.93 (d, 1H, J=4.6 Hz), 4.85 (m, 2H, J=5.0, 10.4, 14.9 Hz). GC-MS (m/z, %): 201/203 (M+, 10), 108 (100).

Preparation of Intermediate (R)-3-(2-Bromo-1-(tert-butyl-dimethyl-silanyl)-ethyl)-pyridine:

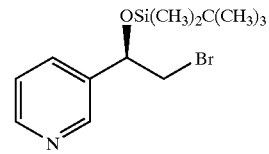

To a stirred solution of 1.54 g (7.61 mmol) of (R)-2-bromo-1-pyridin-3-yl-ethanol in 20 ml of dry N,N-dimethylformamide at room temperature was added 1.55 g (22.83 mmol) of imidazole followed by 1.72 g (11.4 mmol) of tert-butyldimethylsilyl chloride. The mixture was stirred at room temperature for about 18 hours and then an additional 1.55 g (22.83 mmol) of imidazole and 1.72 g (11.4 mmol) of tert-butyldimethylsilyl chloride were added, and the mixture was stirred at room temperature for about an additional 24 hours. The mixture was poured into 200 ml of water and extracted with ethyl acetate (2×200 ml). The organic extracts were combined, washed successively with water (1×40 ml), brine (1×40 ml), then dried over magnesium sulfate and concentrated in vacuo to furnish an oil. Chromatography on silica gel eluting with ethyl acetate:hexanes (2:3, v/v) provided 1.41 g (58% yield) of the desired title compound as a clear oil, $\alpha_D = -51.5$ (c=0.60, chloroform). Chiral HPLC analysis of the product on 4.6× 250 mm Chiralcel® OD column (Chiral Technologies; Exton, Pa.) eluting with hexanes:isopropyl alcohol (7:3, v/v) at 1.0 ml/minute revealed an enantiomeric excess of 91.3%.

$^1$HNMR (400 mHz, CDCl$_3$): δ 8.58 (s, 1H), 8.55 (m, 1H), 7.70 (d, 1H), 7.30 (m, 1H), 4.90 (m, 1H), 3.46 (ddd, 2H, J=1, 2, 7.1, 8.3 Hz), 0.87 (s, 9H), 0.11 (s, 3H). MS (m/z, %): 316/318 (M+, 100).

Preparation of Intermediate 4-Hydroxy-thiobenzamine:

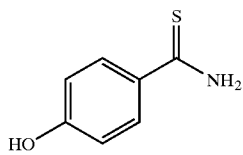

In a round-bottomed flask, 4-hydroxybenzonitrile (5.00 g, 41.9 mmol), diethylthiophosphoric acid (7.02 g, 41.9 mmol), and water (8 ml) were heated with stirring to 80° C. for about thirty minutes. An additional 10 ml of water was then added to the suspension, the reaction mixture was heated for about another one hour, and then was allowed to stir at room temperature for about sixteen hours. The reaction mixture was then extracted with water and 1:1 ether/ethyl acetate. The combined organic extracts were dried over magnesium sulfate, filtered, and concentrated in vacuo. The resulting solid was purified by column chromatography (hexanes to ethyl acetate). The resulting product was isolated as a yellow solid (5.54 g, 87% yield).
$^1$HNMR (400 mHz, CD$_3$OD): δ 6.74 (d, 2H, J=9.1 Hz), 7.83 (d, 2H, J=8.7 Hz).
Preparation of Intermediate 4-(Thiazol-2-yl)-phenol:

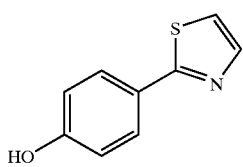

In a round-bottomed flask, bromoacetaldehyde dimethoxyacetal (123 μl, 1.04 mmol), p-toluenesulfonic acid (199 mg, 1.04 mmol), and 4-hydroxy-thiobenzamide (160 mg, 1.04 mmol) were dissolved in ethanol (10 ml) and the resulting solution was heated to reflux for about twenty-four hours. The reaction mixture was then concentrated to an oil which was redissolved in ethyl acetate, and extracted with saturated aqueous sodium carbonate. The combined organic extracts were then washed with brine, dried over magnesium sulfate, filtered, and concentrated in vacuo to an oil. The crude product was purified by column chromatography (hexanes to 10% ethyl acetate/hexanes) to furnish the title compound as a white solid (113 mg, 61% yield). LRMS ([M+H$^+$])=177.8.
Preparation of Intermediate 1-(4-Methoxy-phenyl)-1H-pyrazole:

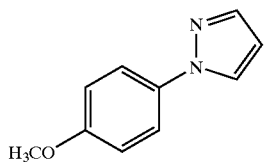

Copper (II) acetate (960 mg, 5.28 mmol) was added to a flame-dried flask charged with pyrazole (240 mg, 3.52 mmol), 4-methoxyphenylboronic acid (1.07 g, 7.04 mmol), 4 A molecular sieves (1.35 activated powder), and pyridine (570 μl, 7.04 mmol) in methylene chloride. The reaction was stirred for approximately two days at room temperature and then filtered through diatomaceous earth. The filtrate was concentrated in vacuo and the residue was purified by column chromatography (isocratic 8% ethyl acetate/hexanes) to furnish 381 mg (2.18 mmol, 62% yield) of the title compound. LRMS ([M+H$^+$])=175.2.
Preparation of Intermediate 4-Pyrazole-1-yl-phenol:

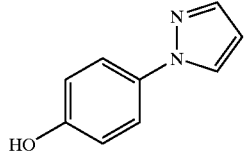

1-(4-Methoxy-phenyl)-1H-pyrazole (400 mg, 2.30 mmol) was dissolved in methylene chloride (8 ml) and the solution was cooled to −78° C. Boron tribromide (1.0 M in methylene chloride, 5.05 ml) was added dropwise to the solution over about five minutes to afford a brown-colored solution. The reaction mixture was allowed to stir for about thirty minutes, the cooling bath was removed, and the mixture was allowed to stir at room temperature for about an additional three hours. The mixture was poured into water, and the resulting mixture was adjusted to about pH 8. The mixture was extracted with methylene chloride (3×25 ml), and the combined organic layers were dried over magnesium sulfate, filtered, and concentrated in vacuo. The resulting crude solid was purified by column chromatography (25% ethyl acetate/hexanes) to afford 183 mg (50% yield) of the desired product as an oil. LRMS ([M+H$^+$])=161.1.
Preparation of Intermediate 4-Pyrazol-3-yl-phenol:

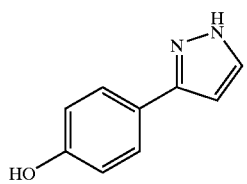

To a round-bottomed flask was added D,L-methionine (1.19 g, 7.96 mmol), 3-(4-methoxyphenyl)-pyrazole (990 mg, 5.68 mmol), and methanesulfonic acid (23 ml). The resulting solution was heated to about 50° C. for about forty-eight hours, and was then allowed to cool to room temperature and poured into water. The pH of the solution was adjusted to about 7 with 5 N sodium hydroxide, and was then extracted with ethyl acetate. The organic extracts were dried over magnesium sulfate, filtered, and concentrated in vacuo to afford 950 mg of a white solid which was determined to be about 95% pure by NMR. This material was subsequently employed directly without further purification.
Preparation of Intermediate [2-(4-Pyrazol-3-yl-phenoxy)-ethyl]-carbamic Acid Benzyl Ester:

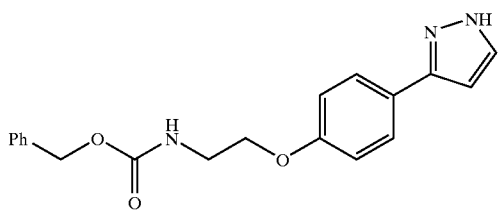

A round-bottomed flask was charged with 4-pyrazol-3-yl-phenol (840 mg, 5.25 mmol), potassium carbonate (2.17 g, 15.7 mmol), and methanesulfonic acid 2-benzyloxycarbonylamino-ethyl ester (C. A. Townsend, et al., Tetrahedron, 47, 2591 (1991)) (2.86 g, 10.5 mmol) in 10.5 ml of dry dimethylsulfoxide. The resulting solution was heated to about 70° C. for about four days. The reaction mixture was then poured into 1 N HCL, and the aqueous phase was extracted twice with ethyl acetate. The combined organic extracts were washed with brine, dried over magnesium sulfate, filtered, and concentrated in vacuo. The crude material was purified by column chromatography (methylene chloride to 2% methanol/methylene chloride) to afford 1.09 g (61% yield) of desired product. LRMS ([M+H$^+$])=338.1.

Preparation of Intermediate [2-(4-Oxazol-4-yl-phenoxy)-ethyl]-carbamic Acid Benzyl Ester:

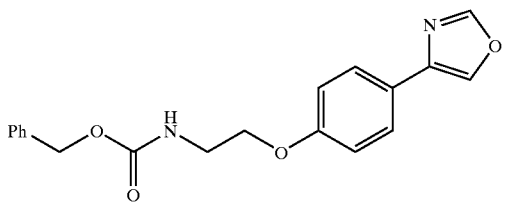

A stirred mixture of 290.0 g (1.80 mol) of 4-oxazol-4-yl-phenol (H. Jones, et al., *J. Med. Chem.*, 21, 1110 (1978)), 737.7 g (2.70 mol) of methanesulfonic acid 2-benzyloxycarbonylamino-ethyl ester, and 746.0 g (5.40 mol) of potassium carbonate in 4.6 l of dry dimethylsulfoxide was heated to about 85° C. An additional 500 ml of dimethylsulfoxide was added and the viscous slurry was stirred at about 80° C. for about an additional two hours. The resulting mixture was cooled to about 50° C., poured into about 1 l of stirred ice water, slurried for about one hour, and then filtered. The wet filter cake was washed with water (2×1 l), and then partially dried by aspiration under vacuum for about two hours. The moist solid was charged into a round-bottomed flask, 6 l of methanol was added, and the mixture was then warmed to about 60° C. where 3 l of water was added. The heating source was removed, the mixture was stirred for about eighteen hours, and then filtered. The filter cake was washed with 2:1 methanol/water (v/v; 2×500 ml), and then dried under vacuum at about 40° C. for about eighteen hours. The title compound (389.5 g, 64% yield) was obtained as a beige powder.

Preparation of Intermediate 2-(4-Oxazol-4-yl-phenoxy)-ethylamine:

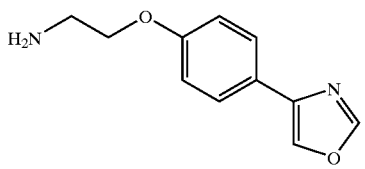

A stirred mixture of 234.0 g (0.692 mol) of [2-(4-oxazol-4-yl-phenoxy)-ethyl]-carbamic acid benzyl ester, 295.1 ml (3.097 mol) of 1,4-cyclohexadiene, and 93.60 g of 10% Pd/C (50% water wet) in 5.6 l of methanol was stirred at room temperature for about twenty-two hours. The mixture was filtered through a pad of diatomaceous earth (13×3 cm), and the filter cake was then washed with 12 l of 100:1 v/v methanol/triethylamine. The filtrate was evaporated in vacuo, and to the residual solid was added 250 ml of toluene. The mixture was stirred at room temperature for about thirty minutes, 2.5 l of hexanes was then added over a period of about five to ten minutes, and the resulting slurry was then stirred for about one hour. The mixture was filtered, and the filter cake was then washed with a mixture of 1:10 toluene/hexanes (3×100 ml), and the solid was dried under vacuum at about 50° C. for about eighteen hours. The title compound (115 g, 81.5% yield) was obtained as a white powder.

Preparation of Intermediate (R)-(2-tert-Butyl-dimethylsilanoxy)-2-pyridin-3-yl-ethyl)-(2-(4-oxazol-4-yl-phenoxy)-ethyl)-amine:

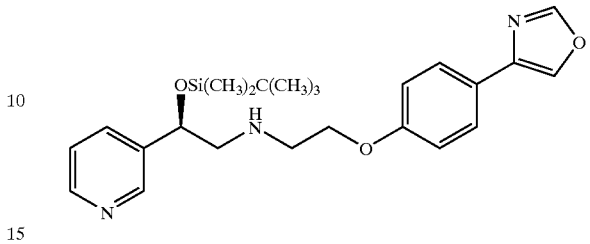

A stirred mixture of 1.24 g (3.91 mmol) of (R)-3-(2-bromo-1-(tert-butyl-dimethyl-silanyl)-ethyl)-pyridine, 1.6 g (7.83 mmol) of 2-(4-oxazol-4-yl-phenoxy)-ethylamine, and 1.4 ml (7.83 mmol) of diisopropylethylamine in 20 ml of dry dimethylsulfoxide was heated at about 90° C. for about 18 hours. The mixture was poured into 400 ml of water and extracted with ethyl acetate (2×400 ml). The organic extracts were combined, washed successively with water (2×100 ml) and brine (1×100 ml), dried over magnesium sulfate, and concentrated in vacuo to furnish an oil. Chromatography on silica gel eluting with methanol:dichloromethane (1:19, v/v) yielded 963 mg (56% yield) of the title compound as an amber-colored oil, $\alpha_D$=−45.7 (c=0.49, chloroform).

$^1$HNMR (400 mHz, CDCl$_3$): δ 8.56 (d, 1H, J=2.1 Hz), 8.50 (dd, 1H, J=1.7, 5.0 Hz), 7.90 (d, 1H, J=0.8 Hz), 7.84 (d, 1H, J=0.8 Hz), 7.65 (m, 3H), 7.26 (m, 2H, 4.85 (dd, 1H, J=3.7, 8.3 Hz), 4.07 (m, 2H), 3.01 (dd, 2H, J=4.6, 6.2 Hz), 2.88 (dd, 2H, J=8.3, 12.0 Hz), 2.76 (dd, 2H, J=3.7, 11.6 Hz), 0.88 (s, 9H), 0.06 (s, 3H). MS (m/z, %): 441 (M$^+$+1, 100).

Example 1

Preparation of (R)-2-(2-(4-Oxazol-4-yl-phenoxy)-ethylamino)-1-pyridin-3-yl-ethanol:

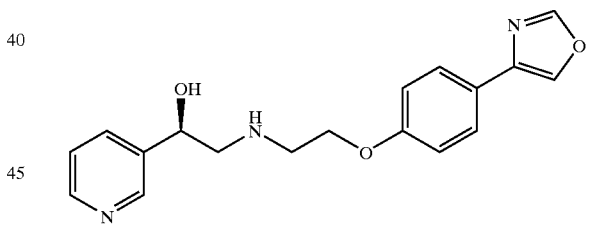

To a stirred solution of 646 mg (1.47 mmol) of (R)-(2-tert-butyl-dimethylsilanoxy)-2-pyridin-3-yl-ethyl)-(2-(4-oxazol-4-yl-phenoxy)-ethyl)-amine in 5 ml of dry tetrahydrofuran at room temperature was added 2.2 ml (2.20 mmol) of 1.0 M tetrabutylammonium fluoride in tetrahydrofuran. The mixture was stirred at room temperature overnight, poured into 100 ml of water, and extracted with ethyl acetate (2×100 ml). The organic extracts were combined, washed successively with water (1×20 ml) and brine (1×20 ml), dried over magnesium sulfate, and concentrated in vacuo to furnish a solid. Chromatography on silica gel eluting with methanol:dichloromethane (1:9, v/v) yielded a solid. Trituration with 10 ml of ethyl acetate:hexanes (1:1, v/v) afforded 250 mg (52% yield) of title compound as a white solid, m.p. 98–100° C., $\alpha_D$=−31.6 (c=0.58, chloroform). Chiral HPLC analysis of the product on 4.6×5 cm Chiralpak AS® column (Chiral Technologies; Exton, Pa.) eluting with acetonitrile:methanol (95:5, v/v) at 1.0 ml/minute revealed an enantiomeric excess of >99.9%.

¹HNMR (400 mHz, d₆-DMSO): δ 8.52 (d, 1H, J=2.1 Hz), 8.47 (d, 1H, J=0.8, 5.0 Hz), 8.41 (dd, 1H, J=1.7,4.6Hz), 8.38 (d, 1H, J=0.8 Hz), 7.70 (m, 3H), 7.30 (m, 1H), 6.96 (ddd, 2H, J=2.5, 4.6, 9.5 Hz), 5.47 (d, 1H, J=3.7 Hz), 4.67 (d, 1H), 4.02 (m, 2H), 289 (t, 2H, J=5.4 Hz), 2.72 (d, 2H, J=6.2 Hz). MS (m/z, %): 326 (M⁺+1, 100).

Anal. Calc'd. for C₁₈H₁₉N₃O₃: C, 66.45; H, 5.89; N, 12.91. Found: C, 66.22; H, 5.92; N, 12.83.

Compounds where HET is a pyrazolyl or a thiazolyl group may be prepared in an analogous process using the appropriate intermediates.

Example 2
Preparation of (R)-2-(2-(4-Oxazol-4-yl-phenoxy)-ethylamino)-1-pyridin-3-yl-ethanol) p-Toluenesulfonate Salt

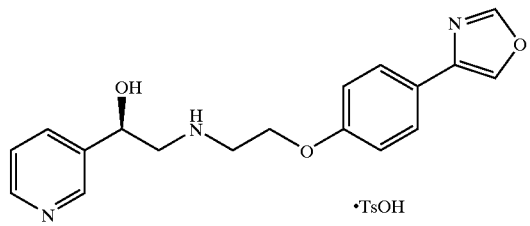

To a stirred solution of 197 mg (0.61 mmol) of (R)-2-(2-(4-oxazol-4-yl-phenoxy)-ethylamino)-1-pyridin-3-yl-ethanol) in 2 ml of methanol at room temperature was added 118 mg (0.61 mmol) of p-toluenesulfonic acid monohydrate. The mixture was stirred at room temperature for about 30 minutes, and then 4 ml of isopropyl ether was added dropwise. The resulting precipitate was stirred for about an additional 15 minutes, filtered, washed with 4 ml of isopropyl ether:methanol (3:1, v/v), and dried to give 225 mg (74% yield) of the title compound as a white solid, m.p. 155.5° C., (α_D=−16.9 (c=0.49, methanol). Chiral HPLC analysis on a 4.6 mm×5 cm Chiralpak AS® column (Chiral Technologies, Exton, Pa.) eluting with acetontrile:methanol (95:5, v/v) at 1.0 ml/minute revealed an enantiomeric excess of >99.9%.

¹HNMR (400 mHz, d₆-DMSO): δ 8.85 (s, br, 2H), 8.59 (d, 1H, J=1.7 Hz), 8.51 (m, 2H), 8.40 (d, 1H, J=0.8 Hz), 7.80 (ddd, 1H, J=1.7, 3.7, 7.9 Hz), 7.72 (ddd, 2H, J=2.9, 4.6, 9.6 Hz), 7.43 (m, 3H), 7.04 (m, 4H), 6.30 (d, 1H, J=4.2 Hz), 5.01 (dd, br, 1H, J=3.3, 7.1 Hz), 4.28 (d, br, 2H, J=5.4 Hz), 3.31 (d, br, 1H, J=12.5 Hz), 3.16 (t, br, J=11.2 Hz), 2.25 (s, 3H), MS (m/z, %): 326 (M⁺+1, 100).

Anal. Calc'd. for C₂₅H₂₇N₃SO₆: C, 60.35; H, 5.47; N, 8.45. Found: C, 60.26; H, 5.48; N, 8.38.

Example 3
Preparation of (R)-2-(2-(4-Oxazol-4-yl-phenoxy)-ethylamino)-1-pyridin-3-yl-ethanol), p-Toluenesulfonate Salt, Monohydrate

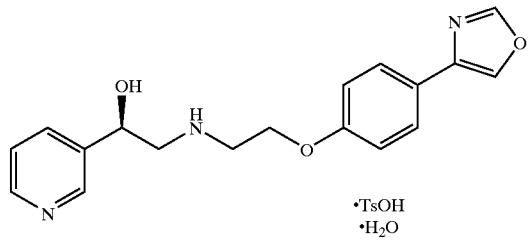

A 1.025 kg sample of (R)-2-(2-(4-oxazol-4-yl-phenoxy)-ethylamino)-1-pyridin-3-yl-ethanol), p-toluenesulfonate salt was slurried in a mixture of 3 l of tetrahydrofuran and 300 ml of water for about eighteen hours. The solid was collected by suction filtration, the filter cake was washed with about 1 l of tetrahydrofuran, and the resulting solid was dried under continued suction for about thirty minutes. The solid was then vacuum dried at a temperature of about 30° C. for about seventy-two hours to afford 768.5 g of the title monohydrate salt.

Anal. Calc'd. for C₂₅H₂₉N₃SO₇: C, 58.47; H, 5.77; N, 8.17; S, 6.36. Found: C, 58.18; H, 5.70; N, 8.12; S, 6.26.

What is claimed is:

1. A process for preparing a compound of the structural formula

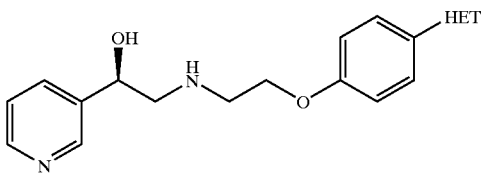

comprising the steps of
(a) reducing an α-bromoketone derivative of the structural formula

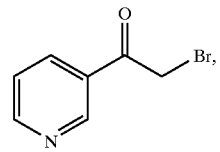

or an acid addition salt thereof, to form an (R)-bromoalcohol derivative of the structural formula

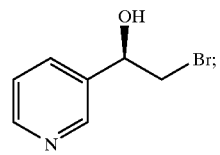

(b) protecting said (R)-bromoalcohol derivative of Step (a) to form an O-protected derivative of the structural formula

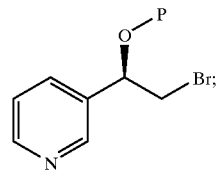

(c) condensing said O-protected derivative of Step (b) with an amine of the structural formula

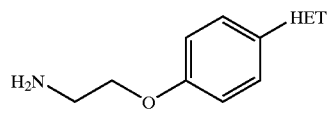

to produce an O-protected derivative of the structural formula

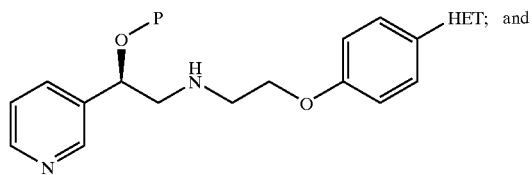

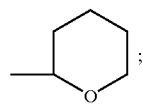

(d) deprotecting said O-protected derivative of Step (c) to form said compound of said structural formula

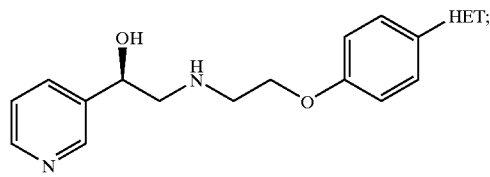

wherein:
  HET is a heterocyclic moiety selected from the group consisting of oxazolyl, pyrazolyl, and thiazolyl; and
  P is an O-protecting moiety selected from the group consisting of —SiR$^1$R$^2$R$^3$, —CH$_2$Ph, —CH$_2$(p-CH$_3$OPh), —CH(OCH$_2$CH$_3$)CH$_3$, and where R$^1$, R$^2$, and R$^3$ are each independently (C$_1$–C$_6$)alkyl, or phenyl.

2. The process of claim 1 wherein said compound formed in Step (d) is isolated as a free base, a pharmaceutically acceptable salt thereof, or a hydrate of said pharmaceutically acceptable salt.

3. The process of claim 1 wherein HET is selected from the group consisting of 2-oxazolyl, 4-oxazolyl, 3-pyrazolyl, 4-pyrazolyl, 2-thiazolyl, and 4-thiazolyl.

4. The process of claim 1 wherein P is —SiR$^1$R$^2$R$^3$, wherein R$^1$, R$^2$, and R$^3$ are each independently (C$_1$–C$_6$) alkyl, or phenyl.

5. The process of claim 4 wherein R$^1$ and R$^2$ are both —CH$_3$, and R$^3$ is —C(CH$_3$)$_3$.

6. The process of claim 1 wherein said reduction Step (a) is mediated by *Absidia cylindrospora* ATCC 22751.

* * * * *